United States Patent [19]
Holroyd

[11] Patent Number: 5,115,778
[45] Date of Patent: May 26, 1992

[54] APPARATUS FOR CONTROLLING AN INTERNAL COMBUSTION ENGINE

[75] Inventor: Trevor J. Holroyd, both of Derby, England

[73] Assignee: Stresswave Technology Limited, Derby, England

[21] Appl. No.: 651,017

[22] Filed: Feb. 5, 1991

[30] Foreign Application Priority Data

Feb. 21, 1990 [GB] United Kingdom ............... 9003878
Aug. 15, 1990 [GB] United Kingdom ............... 9017867

[51] Int. Cl.⁵ .................... G01L 23/22; F02P 5/145
[52] U.S. Cl. .......................... 123/425; 73/35
[58] Field of Search .............. 123/425, 435; 73/35

[56] References Cited

U.S. PATENT DOCUMENTS

| | | | |
|---|---|---|---|
| 4,346,586 | 8/1982 | Furrey | 123/425 X |
| 4,640,250 | 2/1987 | Hosaka et al. | 123/425 |
| 4,710,881 | 12/1987 | Mouri et al. | 123/425 X |
| 4,802,454 | 2/1989 | Tanaka | 123/425 |
| 4,840,158 | 6/1989 | Komurasaki | 123/425 X |

FOREIGN PATENT DOCUMENTS 2053348 2/1981 United Kingdom .
2055468 3/1981 United Kingdom .
2228795 9/1990 United Kingdom .

*Primary Examiner*—Tony M. Argenbright
*Attorney, Agent, or Firm*—Cushman, Darby & Cushman

[57] ABSTRACT

An apparatus for controlling an internal combustion engine comprises a transducer which detects acoustic emissions generated by the operation of the engine, and produces an output signal. The output signal is amplified, rectified and enveloped to produce an electrical signal. The electrical signal has its direct current component removed to leave the alternating current component of the electrical signal. The AC component of the electrical signal is rectified by a rectifier and the mean level of the AC component of the electrical signal is measured by a measurer. An analyzer monitors the mean level of the AC component of the electrical signal and sends a feedback signal to an ignition timing device of the internal combustion engine. The analyzer sends feedback signals such that the mean value of the AC component of the electrical signal lies in the region of a positive peak prior to the occurrence of preignition.

14 Claims, 4 Drawing Sheets

APPARATUS FOR CONTROLLING AN INTERNAL COMBUSTION ENGINE

The present invention relates to an apparatus for controlling an internal combustion engine, particularly for preventing preignition, or knocking, of the internal combustion engine, and/or for operating the internal combustion engine to improve the fuel consumption rate.

It is known to fit electronic ignition controls on internal combustion engines. The lean burn concept was introduced for internal combustion engines to improve efficiency, thereby improving fuel consumption and reducing the amounts of exhaust emissions. The most efficient use of the fuel is made when the ignition timing is advanced as far as possible. However, it is important not to advance the ignition timing too far because preignition, or knocking, is likely to occur. Preignition may cause premature damage to the combustion chamber, or combustion chambers, especially the piston crown, or piston crowns of the internal combustion engine.

There is therefore a requirement for an apparatus for controlling an internal combustion engine to produce maximum fuel efficiency whilst preventing preignition of the internal combustion.

It is known to use accelerometers, which detect vibrations generated by the combustion process, to detect preignition, or knocking, of an internal combustion engine. The accelerometer detects increases in the level of vibrations which are then used to retard the ignition timing of the internal combustion engine.

One disadvantage of the accelerometer preignition detector is that the accelerometer does not give an indication until preignition is actually occurring. Another disadvantage of the accelerometer preignition detector is that it is sensitive to vibrations caused by the ignition of fuel inside the combustion chambers of the internal combustion engine. These vibrations are detected by the accelerometer and the resulting electrical pulse in the output signal dominates the accelerometer output signal during normal operation of the internal combustion engine. Further disadvantages are that considerable signal processing of the accelerometer output is required before the preignition is detected, and severe degrees of preignition are required to provide a sufficient increase in the output level of the accelerometer.

The present invention seeks to provide a novel apparatus for controlling an internal combustion engine which overcomes the above problems.

The present invention provides an apparatus for controlling an internal combustion engine comprising at least one acoustic emission transducer acoustically coupled to the internal combustion engine arranged to detect the acoustic emissions generated during the operation of the internal combustion engine and to produce an output signal corresponding to the level of the acoustic emission activity, means being arranged to rectify and envelope the transducer output signal to produce an electrical signal, means to measure the alternating current component of the electrical signal, means to control the ignition timing of the internal combustion engine, means being arranged to monitor the level of the alternating current component of the electrical signal, the monitoring means being arranged to send a feedback signal to the means to control the ignition timing of the internal combustion engine to adjust the ignition timing to increase efficiency and/or to prevent preignition of the internal combustion engine.

Preferably the means to measure the alternating current component of the electrical signal measures the mean value of the alternating current component of the electrical signal.

Preferably the monitoring means is arranged to send a feedback signal to the means to control the ignition timing of the internal combustion engine such that the means value of the alternating current component of the electrical signal lies in the region of a positive peak level prior to the start of preignition.

Preferably the control means sends a feedback signal to adjust the ignition timing of the internal combustion engine such that the mean value of the alternating component of the electrical signal lies between the positive peak level and a negative peak level of the alternating component of the electrical signal.

Preferably the transducer is arranged to detect acoustic emissions at frequencies greater than 100 KHz.

One transducer may be required for each pair of cylinders in the internal combustion engine.

The transducer may be arranged to detect acoustic emissions at frequencies in the region of 500 KHz.

One transducer may be required for up to four cylinders in the internal combustion engine, the transducer is arranged to detect acoustic emissions at frequencies less than 500 KHz.

The transducer is preferably a resonant transducer.

The control means may send a feedback signal to adjust the ignition timing of the internal combustion engine such that the mean value of the alternating current component of the electrical signal lies on the positive peak level.

The present invention will be more fully described by way of example, with reference to the accompanying drawings in which.

Figure 1:
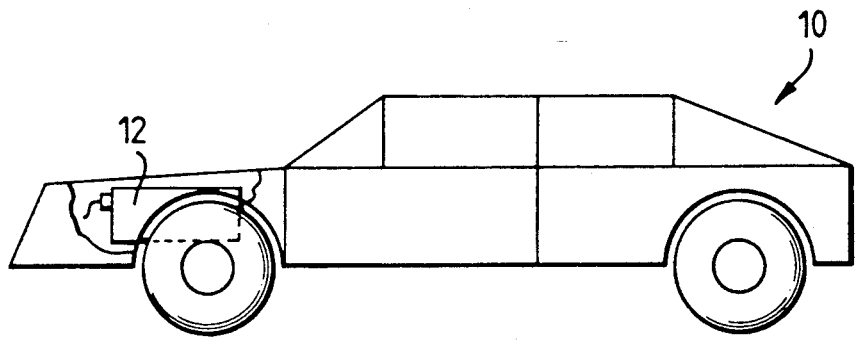
FIG. 1 is a partially cut away view of a motor vehicle having an apparatus for controlling an internal combustion engine according to the present invention.
Figure 2:
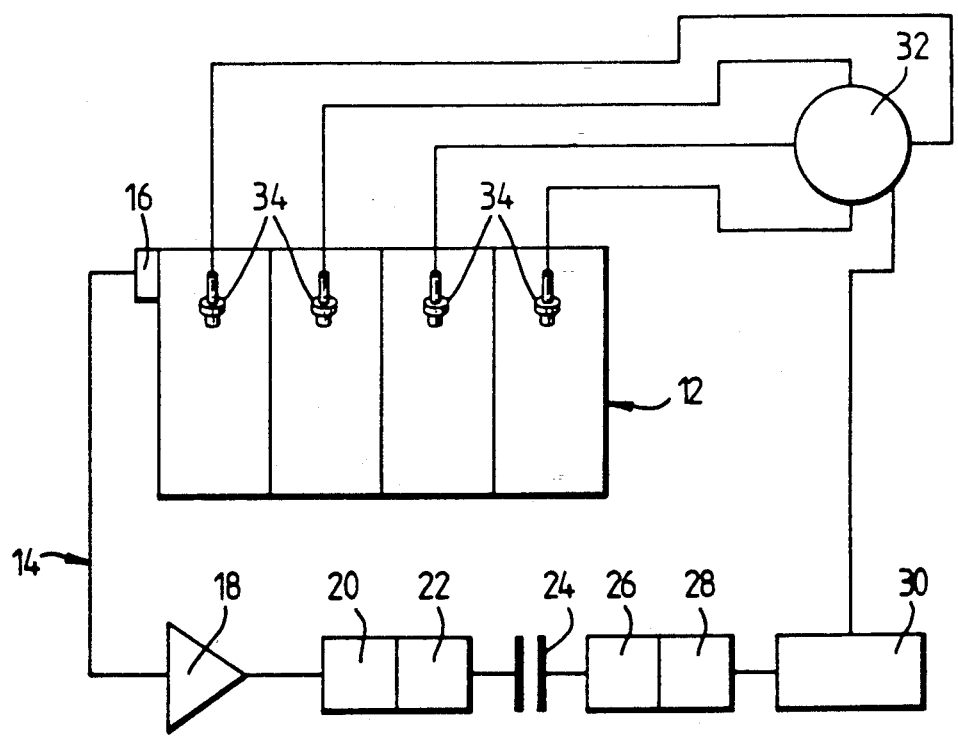
FIG. 2 is an apparatus according to the present invention for controlling an internal combustion engine.

An apparatus 14 for controlling an internal combustion engine 12, of a motor vehicle 10, is shown in FIGS. 1 and 2. The apparatus 14 comprises a transducer 16 which is acoustically coupled to the internal combustion engine 12. The transducer 16 is preferably bolted to the central inlet manifold of the internal combustion engine 12, however it may be bolted onto the engine block at any suitable position. The transducer 16 is a resonant acoustic emission transducer which has a resonant frequency greater than 100 KHz, for example a transducer with a resonant at 500 KHz was used in the following examples. The transducer 16 is arranged to detect the acoustic emissions, or stress waves, generated during the operation of the internal combustion engine and to produce an output signal dependent upon the acoustic emission activity detected. The transducer 16 is commonly a piezoceramic element, although other suitable types of transducer may be used.

The output signal produced by the transducer 16 is supplied to an amplifier 18. The amplifier 18 amplifies the output signal, and may incorporate filters to select the required frequency band or frequency bands if a resonant transducer is not used. The amplified output signal is rectified by a rectifier 20 and then supplied to a signal enveloper 22 which envelopes the rectified output signal. As an example the enveloper 22 envelopes the rectified output signal with a 100 micro second time constant, although other suitable time constants may be selected which allow variations in the electrical signal to be detected, and produces a varying electrical signal.

The varying electrical signal from the enveloper 22, e.g. the enveloped rectified output signal is supplied to a D.C component remover 24 which removes the direct current, D.C., component from the electrical signal to leave an alternating current A.C., component of the electrical signal. The alternating current component of the electrical signal is rectified by a rectifier 26 before passing to a mean level detector 28. The mean level detector 28 measures the mean level of the fluctuations of the rectified alternating current component of the electrical signal. For example the mean level detector 28 is an enveloper which has a 1 second time constant and this integrates the fluctuations in the rectified alternating current component of the electrical signal over the measuring time period. Other suitable time constants may be used which provide slowly varying signals.

The mean level of the fluctuations of the rectified alternating current component of the electrical signal is supplied from the mean level detector 28 to an analyser 30 which monitors this mean level value of the alternating current component of the electrical signal. The analyser 30 is arranged to send a feedback signal to the ignition timing device 32 of the internal combustion engine which causes the ignition timing of the ignition timing device 32 to be adjusted.

In a series of experiments the mean level of the alternating current component of the electrical signal was measured with time at various ignition timing settings. The experiments were conducted with the internal combustion engine operating at substantially constant speed and load, e.g. 1800 revolutions per minute and 80 Nm.

Figure 3:
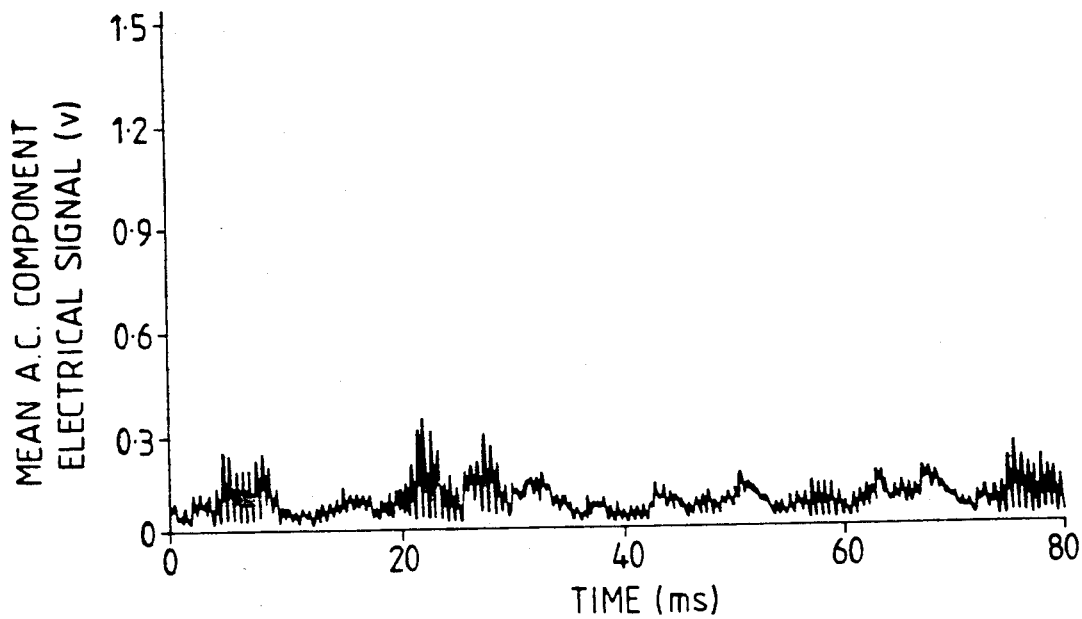
FIGS. 3 to 6 are graphs of the mean value of the alternating current component of the electrical signal level of the present invention against time for various operating conditions of the internal combustion engine.

FIG. 3 shows the mean level of the alternating current component of the electrical signal versus time for the ignition timing set to 8 degrees before top dead centre, the engine speed was 1710 rpm and the load was 80 Nm.

Figure 4:
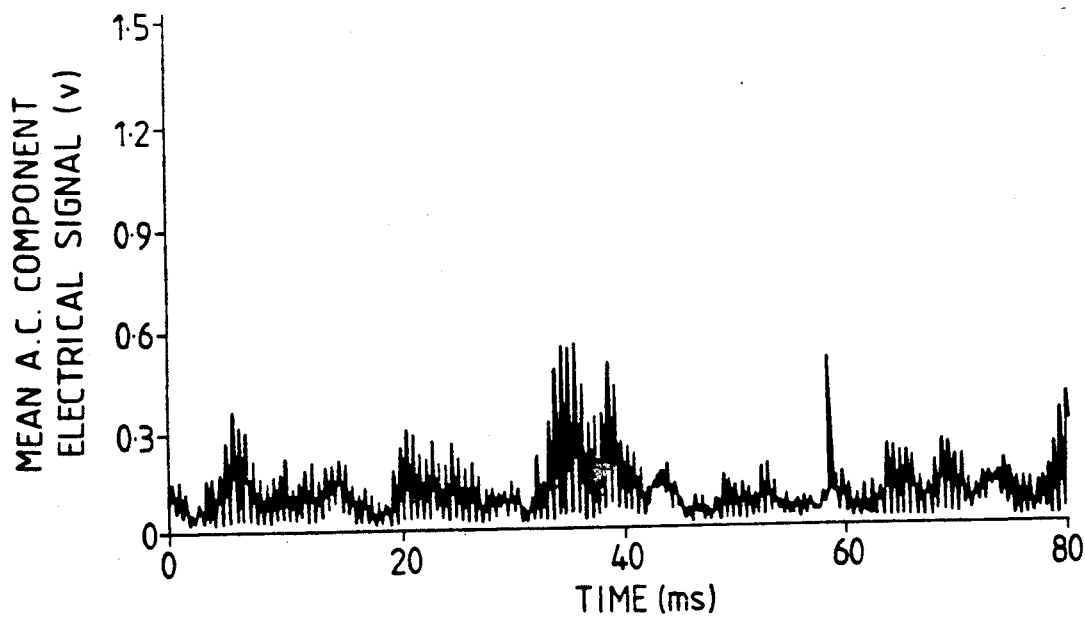

FIG. 4 shows the mean level of the alternating current component of the electrical signal versus time for the ignition timing set to 24 degrees before top dead centre, the engine sped was 2046 rpm and the load was 80 Nm.

Figure 5:
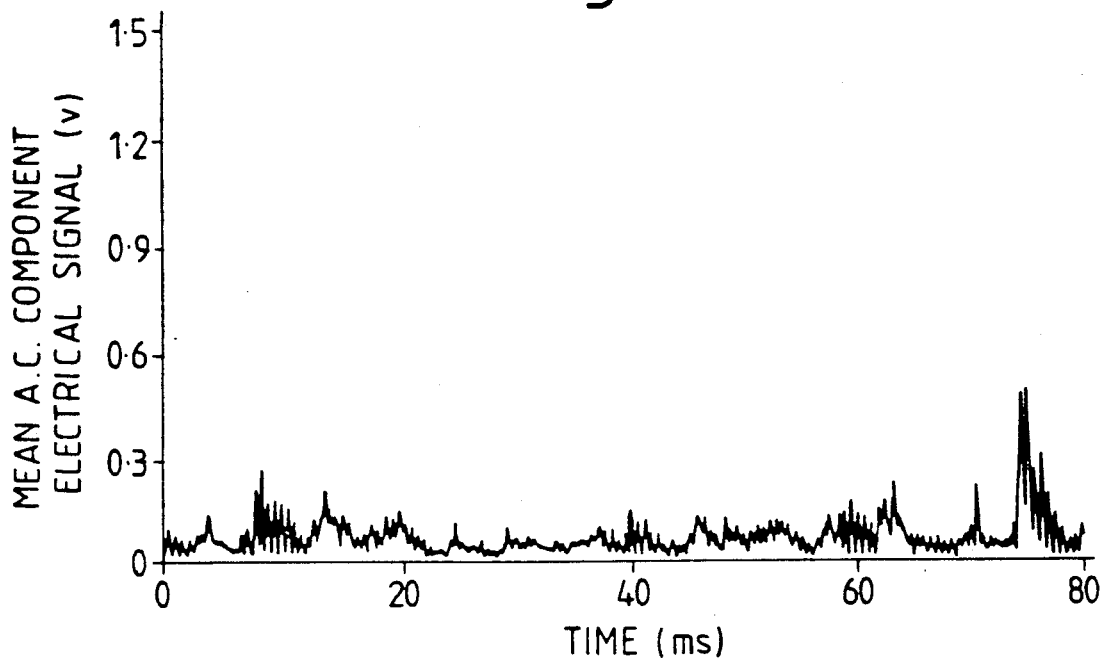
Figure 6:
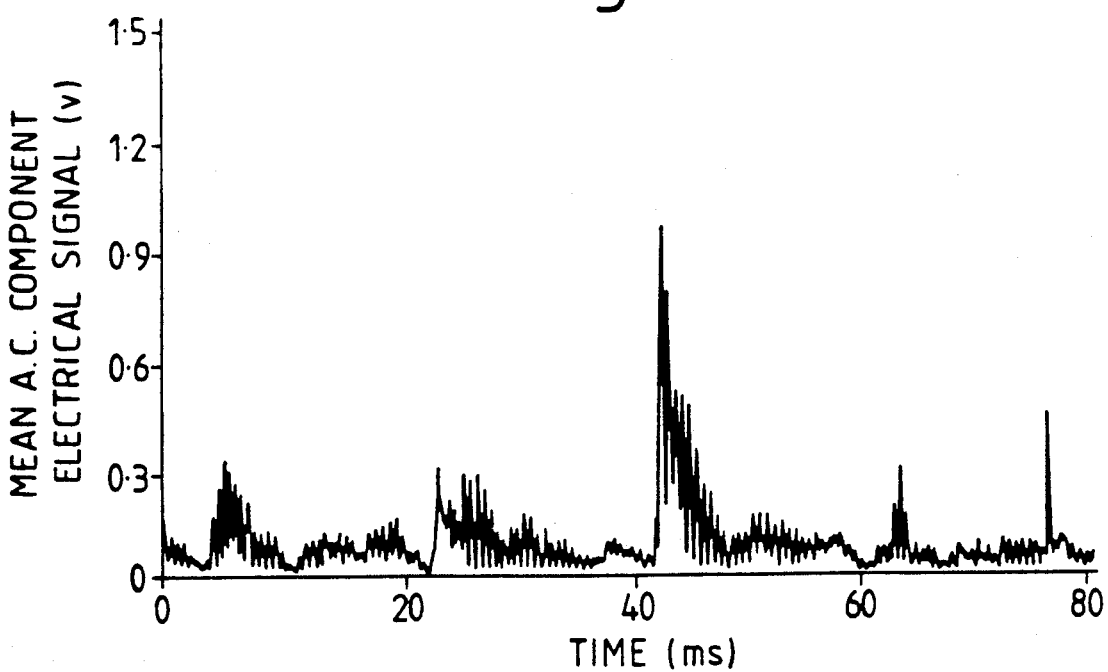

FIG. 5 shows the mean level of the alternating current component of the electrical signal versus time for the ignition timing set to 25 degrees before top dead centre, the engine speed was 1818 rpm and the load was 82 Nm, and FIG. 6 shows the mean level of the alternating current component of the electrical signal versus time for the ignition timing set to 30 degrees before top dead centre, the engine speed was 1590 rpm and the load was 80 Nm.

These graphs indicate that as the ignition timing is advanced the mean level of the alternating current component of the electrical signal reaches a peak level at about 24 degrees before top dead centre and then falls to a minimum at 25 degrees before top dead centre and then increases as the timing is advanced to 0 degrees before top dead centre for substantially constant engine load.

Figure 7:
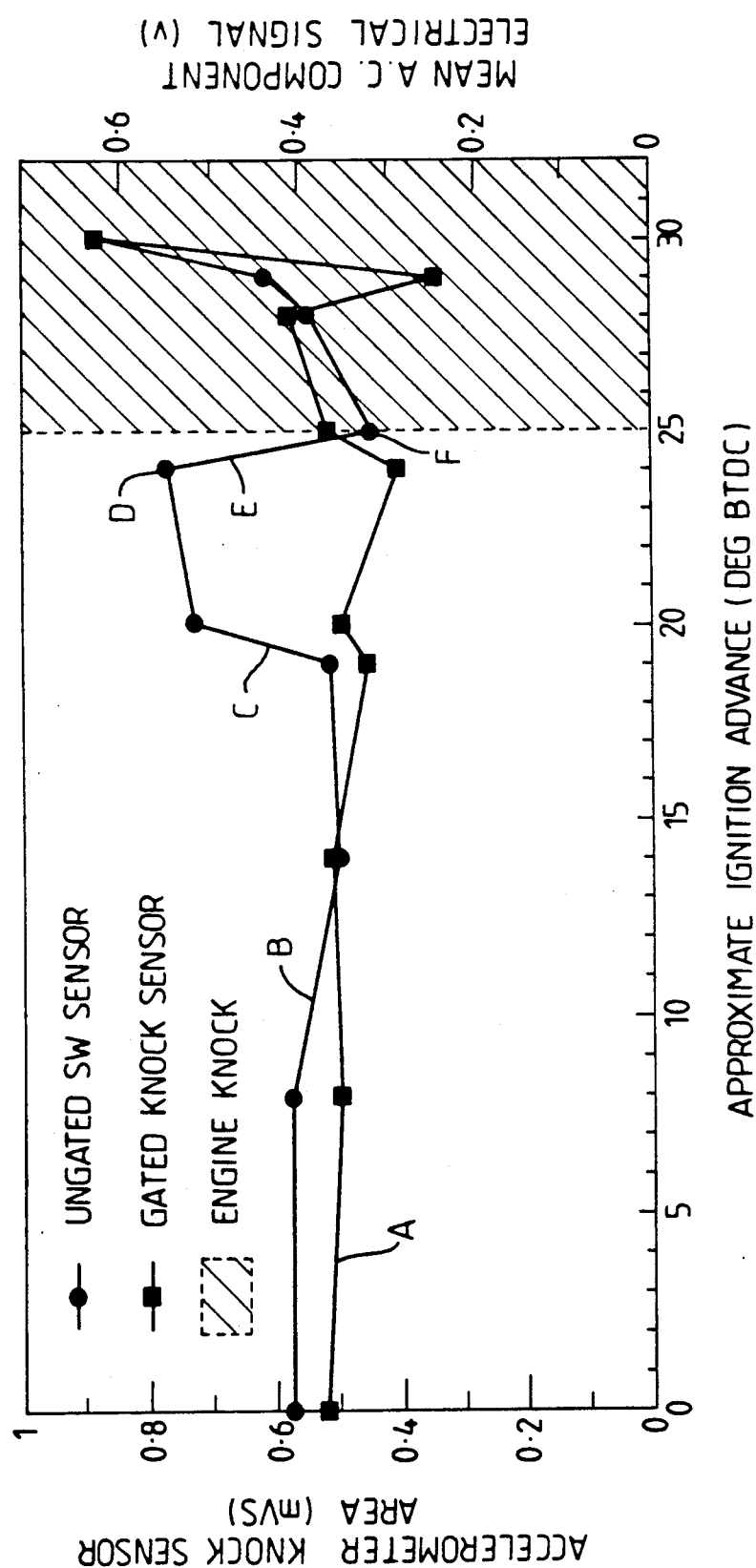
FIG. 7 is a graph comparing the mean value of the alternating current component of the electrical signal level of the present invention against the gated electrical output signal of the prior art accelerometer with various operating conditions of the internal combustion engine.

These results are compared with the output signal of a prior art accelerometer knock detector as shown in FIG. 7 for the same operating conditions as a function of ignition advance, at substantially constant engine load. The shaded area in FIG. 7 indicates the settings of ignition timing for which preignition is audibly detectable. Line A in FIG. 7 indicates the output signal of a gated accelerometer knock detector, and line B indicates the mean alternating current component of the electrical signal from the acoustic emission transducer with different ignition timing.

It is apparent from line A in FIG. 7 that the prior art accelerometer knock detector is not able to detect preignition in the internal combustion engine until it has become quite severe i.e. 30 degrees before top dead centre. The mean level of the alternating current component of the electrical signal in the present invention increases by about 40% in the region immediately prior to knocking/preignition, i.e. between 19 and 25 degrees before dead centre. The most important feature seen from line B of FIG. 7 is the 40% increase in the mean level of the alternating current component of the electrical signal between 19 and 25 degrees before top dead centre. The analyser 30 is arranged to monitor the mean level of the alternating current component of the electrical signal and send a feedback signal to the ignition timing device 32 to adjust the ignition timing of the internal combustion engine 12 until the mean level of the alternating current component of the electrical signal is in the region of the positive peak D between 19 and 25 degrees before top dead centre. The analyser 30 may be arranged to send a feedback signal to the ignition timing device 32 such that the mean level of the alternating current component of the electrical signal is substantially at the positive peak D, or it may be arranged to send a feedback signal to the ignition timing device 32 such that the mean level of the alternating current component of the electrical signal is between the positive peak D and the negative peak F and ensures that it is not at the negative peak F. The feedback signal may be arranged to advance or retard the timing as is appropriate.

The analyser 30 is arranged for example to send feedback signals to the ignition timing device 32 to cause the ignition timing to be adjusted by a predetermined angle, say for example 1 degree. The corresponding change in the mean level of the alternating current component of the electrical signal is analysed to determine if it is at the positive peak D. If it is not at the positive peak D the ignition timing is advanced in increments of 1 degree until the positive peak D is reached if on slope C of line B, or the ignition timing is retarded in increments of 1 degree if on slope E of line B to reach the positive peak D.

The ignition timing is then adjusted to maintain the alternating current component of the electrical signal at the positive peak through changes in engine operating conditions, by dynamically adjusting the ignition timing and monitoring the effect in the alternating current component of the electrical signal, and further adjusting the ignition timing accordingly.

In a similar manner the analyser may be arranged to determine if the alternating current component of the electrical signal is on the slope E between the positive peak D and the negative peak F, and make adjustments to the ignition timing to maintain the alternating current component of the electrical signal on the slope E but to ensure that it is not at the negative peak F because preignition starts to occur at this point.

The present invention is thus able to improve fuel efficiency of the internal combustion engine by controlling the ignition timing and is able to prevent preignition and damage to the combustion chambers. The present invention is able to maintain maximum engine efficiency by maintaining the ignition timing in a region prior to the onset of preignition.

A single transducer may be used to monitor all the combustion chambers, or one transducer may be arranged to monitor a pair of combustion chambers or one transducer may monitor only one combustion chamber. If all combustion chambers are to be monitored from a single transducer the detection frequency of the transducer is arranged to be less than 500 KHz and the transducer is located centrally of the combustion chambers.

A single transducer may be arranged to control each combustion chamber independently using a time filter.

The means to measure the mean level of the alternating current component of the electrical signal measures any suitable statistical measure of the fluctuations in the alternating current component of the electrical signal, for example the standard deviation.

Although reference has been made to an internal combustion engine for a motor vehicle, the invention is applicable to internal combustion engines used for other purposes.

We claim:

1. An apparatus for controlling an internal combustion engine comprising at least one acoustic emission transducer acoustically coupled to the internal combustion engine arranged to detect the acoustic emissions generating during the operation of the internal combustion engine and to produce an output signal corresponding to the level of the acoustic emission activity, means being arranged to rectify and envelope the transducer output signal to produce an electrical signal, means to remove the direct current component from the electrical signal, means to measure the alternating current component of the electrical signal, means to control the ignition timing of the internal combustion engine, means being arranged to monitor the level of the alternating current component of the electrical signal, the monitoring means being arranged to send a feedback signal to the means to control the ignition timing of the internal combustion engine to adjust the ignition timing to increase efficiency of the internal combustion engine.

2. An apparatus as claimed in claim 1 in which the monitoring means is arranged to send a feedback signal to the means to control the ignition timing of the internal combustion engine such that the mean value of the alternating current component of the electrical signal lies in the region of a positive peak level prior to the start of preignition.

3. An apparatus as claimed in claim 2 in which the control means sends a feedback signal to adjust the ignition timing of the internal combustion engine such that the mean value of the alternating component of the electrical signal lies between the positive peak level and a negative peak level of the alternating component of the electrical signal.

4. An apparatus as claimed in claim 1 in which the transducer is arranged to detect acoustic emissions at frequencies greater than 100 KHz.

5. An apparatus as claimed in claim 1 comprising one transducer for each pair of cylinders in the internal combustion engine.

6. An apparatus as claimed in claim 5 in which the transducer is arranged to detect acoustic emissions at frequencies in the region of 500 KHz.

7. An apparatus as claimed in claim 4 comprising one transducer for up to four cylinders in the internal combustion engine, the transducer is arranged to detect acoustic emissions at frequencies less than 500 KHz.

8. An apparatus as claimed in claim 4 comprising means to time filter the transducer output signal to control each combustion chamber independently.

9. An apparatus as claimed in claim 2 in which the monitoring means sends a feedback signal to the control means to adjust the ignition timing of the internal combustion engine such that the mean value of the alternating current component of the electrical signal lies on the positive peak level.

10. An apparatus as claimed in claim 1 in which the means to measure the alternating current component of the electrical signal comprises a rectifier and an enveloper having a long time constant.

11. An apparatus as claimed in claim 10 in which the enveloper has a 1 second time constant.

12. An apparatus as claimed in claim 1 in which the means to rectify and envelope the transducer output signal to produce an electrical signal comprises an enveloper having a short time constant.

13. An apparatus as claimed in claim 12 in which the enveloper has a 100 micro second time constant.

14. An apparatus for controlling an internal combustion engine comprising at least one acoustic emission transducer acoustically coupled to the internal combustion engine arranged to detect the acoustic emissions generated during the operation of the internal combustion engine and to produce an output signal corresponding to the level of the acoustic emission activity, means being arranged to rectify and envelope the transducer output signal to produce an electrical signal, means to remove the direct current component from the electrical signal, means to measure the alternating current component of the electrical signal, means to control the ignition timing of the internal combustion engine, means being arranged to monitor the level of the alternating current component of the electrical signal, the monitoring means being arranged to send a feedback signal to the means to control the ignition timing of the internal combustion engine to adjust the ignition timing to increase efficiency of the internal combustion engine and wherein said means for measuring the alternating current component of the electrical signal measures the mean value of the alternating current component of the electrical signal.

* * * * *